United States Patent [19]
Tucker et al.
[11] 4,442,834
[45] Apr. 17, 1984

[54] PNEUMATIC SPLINT

[75] Inventors: Kevin M. Tucker; Terry L. Sandman, both of Toledo, Ohio

[73] Assignee: Jobst Institute, Inc., Toledo, Ohio

[21] Appl. No.: 307,658

[22] Filed: Oct. 2, 1981

[51] Int. Cl.[3] ............ A61F 5/04
[52] U.S. Cl. ............ 128/90; 128/DIG. 20
[58] Field of Search ............ 128/24 R, 87 R, 89 R, 128/90, 64, 165, 166, 402, 403, 171, 686, 82.1, DIG. 20, 327; 604/141

[56] References Cited

U.S. PATENT DOCUMENTS

| | | | |
|---|---|---|---|
| 3,548,819 | 12/1970 | Davis et al. | 128/82.1 |
| 3,561,435 | 2/1971 | Nicholson | 128/82.1 |
| 3,628,537 | 12/1971 | Berndt et al. | 128/82.1 X |
| 3,871,381 | 3/1975 | Roslonski | 128/24 R X |
| 4,091,804 | 5/1978 | Hasty | 128/64 X |
| 4,156,425 | 5/1979 | Arkans | 128/24 R |
| 4,266,298 | 5/1981 | Graziano | 128/89 R X |
| 4,374,518 | 2/1983 | Villanueva | 128/64 |

FOREIGN PATENT DOCUMENTS

| | | | |
|---|---|---|---|
| 2632088 | 7/1977 | Fed. Rep. of Germany | 128/403 |

*Primary Examiner*—C. Fred Rosenbaum
*Assistant Examiner*—Michelle N. Lester
*Attorney, Agent, or Firm*—Wilson, Fraser, Barker & Clemens

[57] ABSTRACT

The disclosure relates to a pneumatic splint formed of three similarly shaped walls of flexible thermoplastic material. The inner and outer walls are of identical shape and are peripherally bonded to each other. The intermediate wall is of lesser peripheral dimension and has three of its edges bonded to corresponding edges of the inner and outer walls and the fourth edge bonded to an intermediate portion of the outer wall. The intermediate wall is provided with a plurality of spaced apertures and a plurality of equally spaced welded bonds to the outer wall. The application of fluid pressure to the interior of the splint when rolled into an annular configuration to loosely surround a human limb will expand the inner wall into intermittent engagement with the limb and the outer wall into a uniform, quilted cushion configuration.

5 Claims, 7 Drawing Figures

PNEUMATIC SPLINT

BACKGROUND OF THE INVENTION

1. Field of the Invention

The invention relates to pneumatic splinting devices, particularly those used for the management of post-operative edema associated with the amputation of a human extremity, such as the leg, and those used to assist the early post-operative ambulation of an amputee.

2. Description of the Prior Art

Pneumatic splints were heretofore fabricated by sealing the perimeter of two sheets of non porous, flexible material, thus forming inner and outer walls which could be wrapped around the human limb to which the splint was to be applied and then the chamber defined between the inner and outer walls was filled with low pressure air to immobilize the device and the enclosed limb.

While this construction is adequate for use as a short term emergency splint to immobilize fractures occuring in the extremities, it has pronounced disadvantages when an attempt is made to employ the device for a longer period of time, as required in the post amputation management of edema and early ambulation of the amputee. The two layer construction, when applied to a human limb or extremity and inflated by air, tends to mishape and apply non-uniform pressure to the surrounded limb, which results in a reduction of effective edema control and reduces the protective cushioning effect of the surrounding envelope formed by the inflated device. Since the expansion of the outer layer is limited solely by the tensile strength of the material, any non-uniformity in such tensile strength results in excessive localized expansion and reduced rigidity of the inflated device, which in turn reduces the supportive action of the device and hence its effectiveness as a ambulatory aid. Lastly, conventional pneumatic splints formed of two peripherally sealed layers normally result in the formation of a gap or channel running the length of the device in the area where the fastening means are attached to the device which hold the device in its annular configuration. This channel of reduced inflation forms an area into which the limb extremity is forced by the greater inflation of the remainder of the device, thereby resulting in that portion of the limb extremity being both unsupported and relatively uncushioned by the device.

Typical prior art pneumatic splints formed by the peripheral bonding of two layers of nonpervious material are disclosed in U.S. Pat. Nos. 2,823,668, 3,824,992 and 4,156,425.

SUMMARY OF THE INVENTION

This invention provides a pneumatic splint comprising a three wall device which define two pneumatic chambers between the respective walls, which chambers are interconnected by apertures provided in the intermediate wall. The inner wall is formed from a thermoplastic sheet material by cutting a quadrilateral shape which, when rolled about a human limb or limb extremity will define a loosely fitting annular wall with the longitudinal edges of such wall preferably disposed in overlapped relationship. An intermediate and an outer wall member are fabricated from the same thermoplastic sheet material and are of similar configuration to the inner member. The outer wall has an identical shape as the inner wall. The intermediate wall is of lesser peripheral dimension to define a peripheral flap on said inner and outer walls extending beyond the one longitudinal edge of said intermediate wall which is peripherally bonded to the inner and outer walls. Thus when the assembly is rolled around a limb, the peripheral flap portions overlap the outer wall. A zipper half or strip of fastening material is secured to the inner face of the peripheral flap portion and a cooperating zipper half or strip of fastening material is secured to the outer surface of the outer wall to hold the assembly in its rolled position.

A first pneumatic chamber is defined between the inner wall and the intermediate wall. A second fluid chamber is defined between the intermediate wall and the outer wall. Fluid communication is provided between the first and second chambers by a plurality of spaced apertures formed in the intermediate wall member. An appropriate fixture and valve for supplying and retaining air or other suitable fluid within the chambers is fastened to the exterior of the outer wall.

The outer wall is further bonded to the intermediate wall at a plurality of spaced regions intermediate the apertures in the intermediate wall. Thus, when fluid pressure is applied to the first and second chambers, the inner wall is expanded inwardly into snug, uniform engagement with the human limb or limb extremity. The outer wall is concurrently expanded outwardly, but such expansion is limited to a substantially uniform configuration by the plurality of spaced bonds between the outer wall and the intermediate wall. Thus, a uniform pressure is applied to all portions of the human limb or limb extremity and a substantially uniformly shaped cushion is defined around the limb by the fluid confined between the inner, intermediate and the outer walls.

Further objects and advantages of the invention will be readily apparent to those skilled in the art from the following detailed description, taken in conjunction with the annexed sheets of drawings, on which is shown a preferred embodiment of the invention.

DESCRIPTION OF THE PREFERRED EMBODIMENTS

Figure 1:
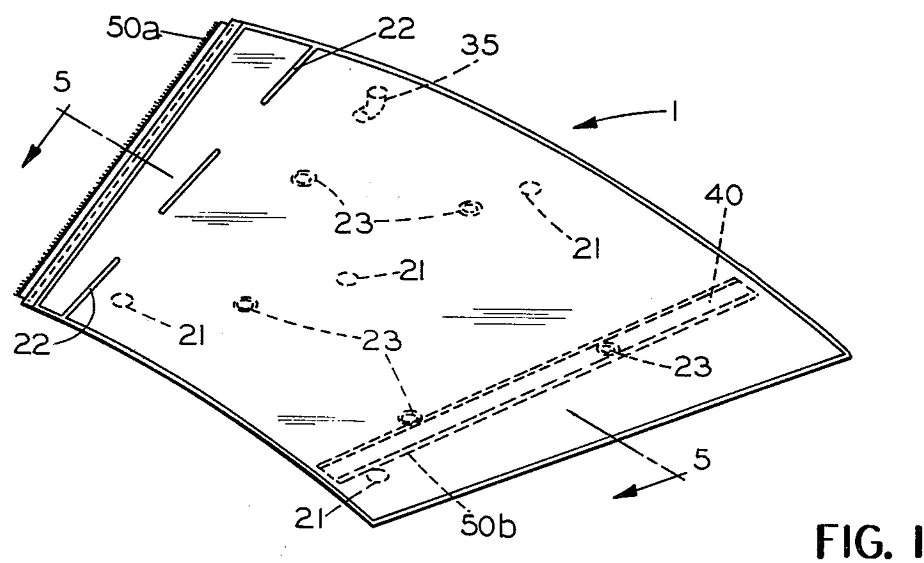
FIG. 1 is an elevational view of an assembled three wall pneumatic splint embodying this invention.
Figure 5:
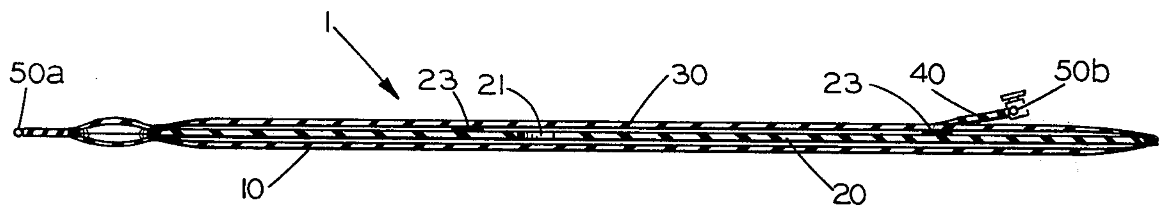
FIG. 5 is a sectional view taken on the plane 5—5 of FIG. 1.

A pneumatic splint 1 embodying this invention comprises an assemblage of three wall elements, respectively an inner wall 10, an intermediate wall 20 and an outer wall 30. Each of the aforesaid wall elements is cut from a sheet of impervious, flexible thermoplastic material, for example polyurethane sheet having a thickness of the order of 10 mills.

The inner wall 10 and the outer wall 30 are of identical shape and comprise generally frusto-conical quadrilaterals having peripheral edges 10*a*, 10*b*, and 30*a*, 30*b*, and longitudinal edges 10*c*, 10*d* and 30*c*, 30*d*.

The intermediate wall 20 is fabricated from the same thermoplastic sheet material, but is of lesser peripheral extent than the inner and outer walls 10 and 30. Additionally, the intermediate wall 20 is provided with a plurality of spaced apertures 21 which are disposed across the surface of the sheet.

Intermediate wall 20 is peripherally bonded to the outer wall 30 by conventional heat sealing techniques. Thus, the two peripheral edges 20*a* and 20*b* of the intermediate wall 20 are bonded to the corresponding edges 30*a* and 30*b* of the outer wall. The one longitudinal edge 20*c* is bonded to the corresponding longitudinal edge 30*c* but the other longitudinal edge 20*d* of the intermediate wall 20 is bonded to an intermediate portion of the outer wall 30 by a series of a disconnected line bonds 22.

For a purpose to be hereinafter described, the intermediate wall 20 is further bonded to the outer wall 30 at a plurality of substantially equally spaced regions by spot welds 23. After the spot welds 23 are produced, the combined intermediate wall 20 and outer wall 30 are then united to the inner wall 20 by peripherally bonding all edges of the inner wall 10 to the corresponding edges of the outer wall 30. The disconnected line bonds 22 are also applied to inner wall 10.

There is thus defined a unitary structure which, when rolled about a human extremity, forms a generally frusto-conical, annular configuration and defines two separate chambers 15 and 25 respectively disposed between inner wall 10 and the intermediate wall 20 and between intermediate wall 20 and the outer wall 30. The chambers 15 and 25 are freely interconnected for the passage of fluid by the spaced apertures 21 provided in the intermediate wall 20.

To inflate the chambers 15 and 25, a conventional air valve 35, similar to that employed on pneumatic tires, is suitably secured to the outer face of the outer wall 30. Low pressure fluid, such as air, may then be supplied through the valve 35 to each of the chambers 15 and 25, resulting in the inward expansion of the inner wall 10 against the human limb around which the splint is wrapped and the outward expansion of the outer wall 30 to provide cushioned protection of the surrounded limb. The plurality of equally spaced spot welds 23 provided between the intermediate wall 20 and the outer wall 30 limits the expansion of the outer wall 30 so that it maintains a substantially uniform, although quilted, configuration.

To secure the pneumatic splint 1 around the limb to be treated, any conventional form of fastening means may be provided between the peripheral portions of the inner wall 10 which overlap the outer wall 30. The splint is normally designed so that all of the peripheral portions 10*c* and 30*c* of inner wall 10 and outer wall 30 which lie peripherally beyond the edge 20*d* of the intermediate wall, overlap the longitudinal edges 10*d* and 30*d* when rolled about the limb. The employment of interrupted line bonds 22 between the intermediate wall 20 and both the outer wall 30 and the inner wall 10 assures that the pneumatic fluid enters the overlapping peripheral portions 10*d* and 30*d* of the inner wall 10 and the outer wall 30. It is therefore assured that when the splint is wrapped around a limb or limb extremity, the pneumatically cushioned inner wall 10 is in complete contact with the entire periphery of the limb or limb extremity and there is no longitudinal gap in the fluid pressure wall contact with the limb due to the fastening means.

Figure 6:
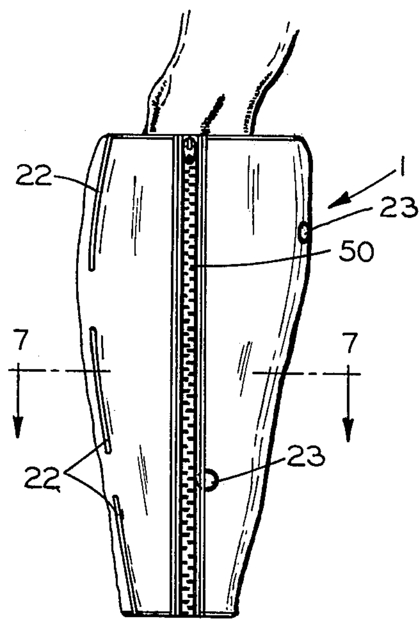
FIG. 6 is a schematic elevational view illustrating the assemblage of a splint embodying this invention to an extremity of a human limb.
Figure 7:
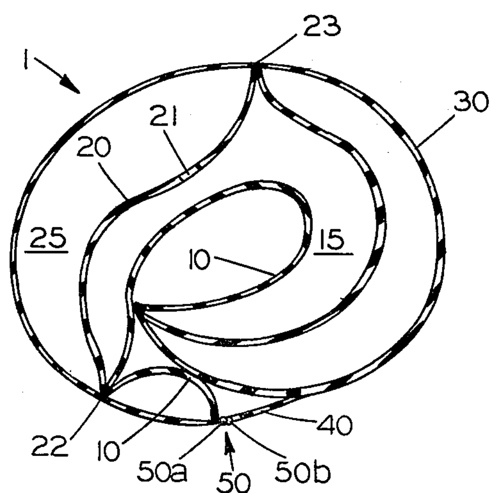
FIG. 7 is a sectional view taken on the plane 7—7 of FIG. 6.
Figure 2:
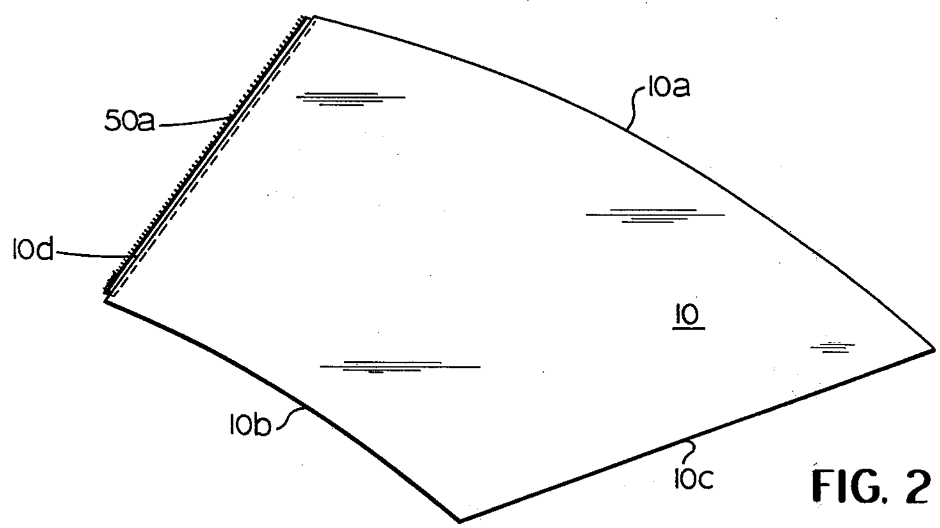
FIG. 2 is an elevational view of the inner wall of the three wall pneumatic splint of FIG. 1.
Figure 4:
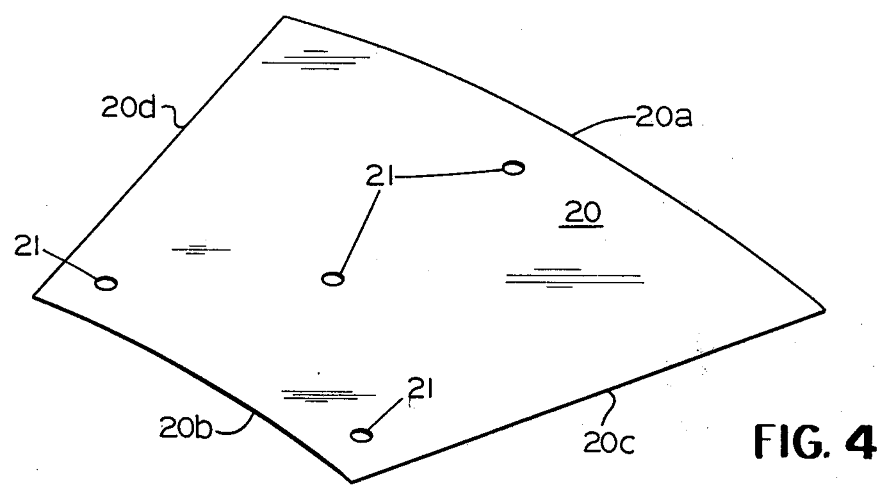
FIG. 4 is an elevational view of the intermediate wall of the three wall pneumatic splint of FIG. 1.
Figure 3:
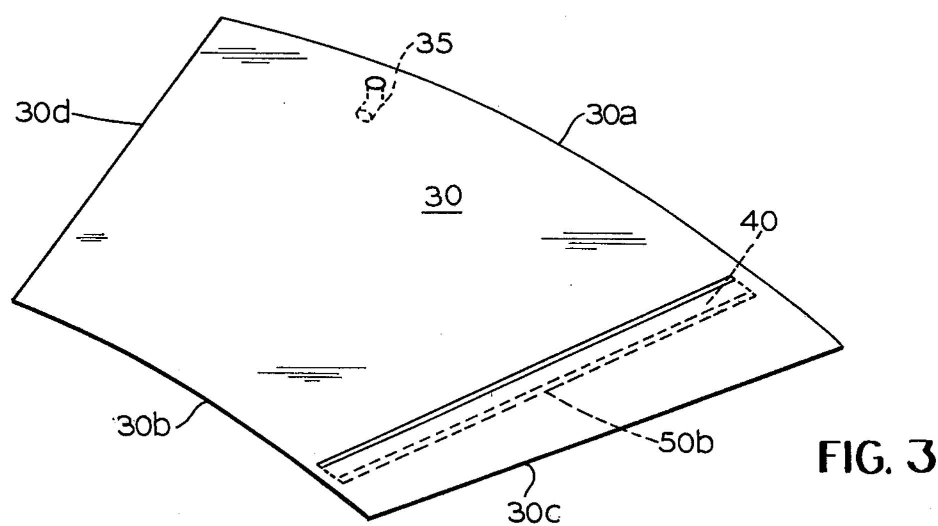
FIG. 3 is an elevational view of the outer wall of the three wall pneumatic splint of FIG. 1.

The fastening means 50 provided may comprise a plastic zipper which is conventionally formed in two parts 50*a* and 50*b* which are respectively bonded to the longitudinal edges 10*d* and 30*c* of the inner and outer walls 10 and 30 and to a thermoplastic flap 40 which is heat sealed or bonded to the outer wall 30 on the same face of such outer wall as the air valve 35. The wrapping of the pneumatic splint assemblage 1 around the human limb or limb extremity brings the two half portions 50*a* and 50*b* of the zipper 50 into proximity and the zipper 50 may then be secured as indicated in FIG. 6. Alternatively, strips of the well known plastic hook and eye fastening materials sold under the trademark "Velcro" may be substituted for the zipper halves 50*a* and 50*b* and such strips effect the securement by being brought into overlapping engagement when the pneumatic splint is wrapped around the human limb or limb extremity.

From the foregoing description, it is apparent that the described pneumatic splint provides an assured fluid pressure contact around all portions of the enclosed human limb. Moreover, the external configuration of the pneumatic splint, when inflated, is limited to the generally frusto-conical configuration illustrated in FIG. 6 by virtue of the securement of spaced regions of the outer wall 30 to the intermediate wall 20 by the equally spaced spot welds 23. Obviously, the splint may be readily applied to the human limb by merely wrapping it around the limb and either fastening the zipper halves 50*a* and 50*b*, or engaging the "Velcro" strips if that type of fastening means is employed. The splint is then inflated by supplying low pressure air through the valve 35. The pressure within the splint may be varied in a well known manner if control of edema by a fluctuating pressure is desired.

Modifications of this invention will be readily apparent to those skilled in the art and it is intended that the scope of the invention be determined solely by the appended claims.

What is claimed is:

1. A pneumatic splint comprising an inner wall, an intermediate wall, and an outer wall, each of said walls being formed of thermoplastic sheet material and adapted to be rolled into an annular configuration to loosely surround a human limb; both peripheral edges and one longitudinal edge of said intermediate wall being bonded to respective peripheral and longitudinal edges of said outer wall and a second longitudinal edge of said intermediate wall being bonded to an intermediate portion of said outer wall so as to define a first air chamber therebetween; said intermediate wall having a plurality of spaced apertures therein and being bonded to said outer wall at localized regions spaced apart from said apertures; said outer wall being substantially identical in shape to said inner wall and having its peripheral and longitudinal edges respectively bonded to the peripheral and longitudinal edges of said inner wall to define a second air chamber between said inner and intermediate walls; one peripheral end portion of the inner surface of said outer wall lying in overlapped abutting relation to a peripheral end portion of the outer surface of the inner wall when said walls are rolled into said annular configuration; means on said outer wall for supplying and maintaining pressured air in said second chamber so as to maintain said inner wall in spaced apart relation to said intermediate wall such that a substantially uniform pressure is applied against the human limb when inflated; and fastening means on said overlapped abutting peripheral end portions of said outer wall and said inner wall for detachably securing said end portions in overlapped relation when said walls are rolled into said annular configuration.

2. The pneumatic splint of claim 1 wherein said localized regions comprise spot welds substantially equally spaced from each other and disposed over the entire surface of said intermediate wall.

3. The pneumatic splint of claim 1 or 2 wherein said second longitudinal edge of said intermediate wall is bonded to said outer wall by an interrupted line seal.

4. The pneumatic splint of claims 1 or 2 wherein said fastening means comprising cooperating strips of hook and eye material respectively secured to the outer wall and the overlapping peripheral edge surface of said inner wall.

5. The pneumatic splint of claims 1 or 2 wherein said fastening means comprises zipper half portions respectively secured to the outer wall and the overlapping peripheral edge surface of said inner wall.

* * * * *